United States Patent [19]
Fischer et al.

[11] Patent Number: 5,722,833
[45] Date of Patent: Mar. 3, 1998

[54] VISCOUS NEUTRALIZING BARRIER

[75] Inventors: Dan E. Fischer, Sandy; Steven D. Jensen, Riverton, both of Utah

[73] Assignee: Ultradent Products, Inc., South Jordan, Utah

[21] Appl. No.: 667,915

[22] Filed: Jun. 20, 1996

Related U.S. Application Data

[63] Continuation-in-part of Ser. No. 408,812, Mar. 21, 1995, Pat. No. 5,700,148.
[51] Int. Cl.$^6$ .................................................. A61C 5/00
[52] U.S. Cl. ........................... 433/217.1; 216/49; 216/51
[58] Field of Search .......................... 433/215, 217.1, 433/226, 227, 228; 216/49, 50, 51; 156/659.11; 106/35; 523/116, 117

[56] References Cited

U.S. PATENT DOCUMENTS

| | | | |
|---|---|---|---|
| 4,443,197 | 4/1984 | Fusayama et al. | 433/217 |
| 4,719,149 | 1/1988 | Aasen et al. | 428/473 |
| 5,385,728 | 1/1995 | Suh | 424/54 |
| 5,498,643 | 3/1996 | Antonucci et al. | 523/118 |

*Primary Examiner*—Cary E. O'Connor
*Attorney, Agent, or Firm*—Workman Nydegger Seeley

[57] ABSTRACT

A syringe-deliverable neutralizing barrier and methods for delivering a composition to form the neutralizing barrier. The neutralizing barrier is formed from a viscous caulking-type material delivered onto a tooth surface to define an etching area while protecting surrounding dental tissues during the application of an etching composition. The caulking-type material includes a matrix material and a neutralizing agent and has a viscosity such that it is syringe-deliverable yet will intimately and continuously adhere to the tooth surface without substantially flowing after being placed in a desired configuration. The neutralizing barrier is generally water soluble in order to facilitate quick and easy rinsing of the etching composition and neutralizing barrier in order to terminate the etching process, and preparatory to subsequent bonding of a porcelain crown or resinous composite to the tooth or porcelain prosthesis. The neutralizing barrier is particularly useful with etching compositions containing hydrofluoric acid, but can be used for other relatively strong tooth etchants.

41 Claims, 2 Drawing Sheets

VISCOUS NEUTRALIZING BARRIER

RELATED APPLICATION

This application is continuation-in-part patent application of U.S. patent application Ser. No. 08/408,812 filed on Mar. 21, 1995, U.S. Pat. No. 5,700,148, in the names of Dan E. Fischer, D.D.S. and Steven D. Jensen and entitled Syringe-Deliverable Neutralizing Barrier. For purposes of disclosure this application is hereby incorporated specifically by reference.

THE FIELD OF THE INVENTION

The present invention relates to compositions and methods for preparing a surface of a tooth, porcelain prosthesis, metal or other material conducive to acid etching or conditioning. More particularly, the present invention is directed to a syringe-deliverable composition that forms a neutralizing barrier whereby a selected area of a tooth surface is isolated for etching, while protecting the surrounding tooth area, sulcular tissue and gums from the acid etch. The neutralizing barrier is particularly well-suited for procedures that involve the controlled etching of a porcelain surface of tooth prosthesis or crown with hydrofluoric acid preparatory to the application of a new crown or composite material over the porcelain surface.

THE PRIOR STATE OF THE ART

Since the advent of porcelain crowns, resinous composites, and sealant materials that can be applied to tooth surfaces, as well as existing porcelain or other composite tooth prostheses, an important procedure was insuring a strong bond between the newly applied crown, resinous composite or sealant and the existing tooth or porcelain prosthesis. Although enamel, and to a certain degree dentin, can be acid etched in order to promote bonding thereto, existing prostheses such as porcelain based crowns or bridges are resistant to typical acid etches used to prepare enamel or dentin surfaces.

In general, the strength of the bond between an existing tooth and a resinous composite or sealant material is greatly increased by forming mechanical undercuts to the desired area of the tooth onto which the resinous material is to be bonded. The tooth surface is typically conditioned or etched by applying an aqueous acid solution onto the surface of the tooth to be etched. Fairly strong acids such as hydrochloric or nitric acid can be used to prepare metal or porcelain tooth surfaces, although phosphoric acid is usually preferred for tooth etching due to its relatively lower toxicity.

Although hydrofluoric acid (HF) is known to effectively etch porcelain surfaces, it has heretofore been difficult to employ hydrofluoric acid etches on existing porcelain prostheses within a patient's mouth due to the extremely hazardous nature of hydrofluoric acid. Hydrofluoric acid is known to cause severe and immediate deterioration of surrounding sulcular and gum tissues onto which the hydrofluoric acid can easily run during the etching process. This is particularly true in the case where a substantial portion of the damaged prosthetic tooth has been cut away so that the porcelain surface to be etched is even closer to the surrounding sulcular and gum tissues. Attempts have been made to protect the surrounding tissues by the use of various mechanical barriers such as cotton rolls, rubber dam caulking, or other conventional isolation techniques. Many times, however, these mechanical barriers are inappropriate due to the need for the etching to occur in the subgingival area.

Although acids used to etch enamel and dentin pose a smaller risk to surrounding sulcular and gum tissues compared to hydrofluoric acid, they still can cause substantial irritation if allowed to contact the surrounding tissues for any significant length of time.

In general, contact between an acid etch and the cheeks and tongue of a patient can be minimized through the use of cotton rolls, absorbent isolators, rubber dams or other conventional isolation techniques. The gums, adjacent dentin and surrounding sulcular tissues however are harder to protect from the acid etch due to their close proximity to the surfaces being etched and because the etch is usually a somewhat to freely flowable aqueous solution. Although it is possible to incorporate the acid etches within a gel in order to inhibit the unwanted flow of the etching solution from the desired etching area, they generally must have a low enough viscosity to flow into the tiny crevices and other irregularities of the surface of the tooth or prosthesis being etched. Hence, it is generally impractical to have an acid etch that is so viscous that it is not at least partially flowable.

Besides adjusting the flow characteristics, the concentration of the etching solution can be modified to reduce the damage caused by inadvertent contact with surrounding sulcular and gum tissues. However, significantly reducing the concentration of the etching solution also reduces its ability to etch the surface being treated, thereby increasing the time in which the acid etch must remain in contact with the surface being treated. In general, etching solutions strong enough to adequately etch tooth surfaces will also damage and irritate surrounding soft gum tissues.

In light of the foregoing, it would be a significant advancement in the art to provide compositions and methods for protecting sulcular and gum tissues surrounding a tooth or prosthetic implant being etched.

It would be a further advancement in the art to provide compositions and methods that resulted in a quickly and easily applied barrier to maintain an etching solution within the area of the tooth or prosthetic porcelain surface that is desired to be etched.

It would yet be an additional advancement in the art to provide compositions and methods that allowed for the direct application of hydrofluoric acid to existing porcelain prosthetic tooth implants, while simultaneously protecting surrounding hard or soft tissues from damage or undesirous exposure.

It would yet be an improvement in the art to provide compositions and methods that provided for the neutralization of any hydrofluoric acid or other acid etching solution that came in contact with the barrier protecting the surrounding sulcular and adjacent gum tissues.

Finally, it would be a further advancement in the art to provide compositions and methods that yielded a barrier that could be quickly and effectively rinsed away with water along with the etching solution in order to terminate the etching procedure and quickly clean the etched surface preparatory to subsequent bonding.

Such compositions and methods for protecting sensitive tissues surrounding a tooth or porcelain prosthetic implant being etched are disclosed and claimed herein.

SUMMARY AND OBJECTS OF THE INVENTION

The present invention has been developed in response to the present state of the art and, in particular, in response to problems and needs that have not been fully or completely solved by compositions and methods for preparing a tooth or porcelain prosthesis for subsequent bonding with a new crown or resinous composite. Thus, it is an overall object of the present invention to provide a neutralizing barrier and methods for delivering a neutralizing barrier for use in acid etching the surface of a porcelain prosthesis or tooth in order to prepare the porcelain prosthesis or tooth for bonding wherein the barrier is preferably syringe-deliverable.

It is a primary object of the present invention to provide a neutralizing barrier and methods for delivering a neutralizing barrier in order to isolate tooth tissues and/or protect sulcular and gum tissues surrounding a tooth or prosthetic implant being etched.

Another object of the present invention is to provide a quickly and easily applied syringe-deliverable neutralizing barrier and methods for delivering the neutralizing barrier in order to maintain an etching composition within the area of the tooth or prosthetic porcelain surface that is desired to be etched.

Yet another object of the present invention is to provide a neutralizing barrier and methods for delivering a neutralizing barrier in order to directly apply hydrofluoric acid to existing porcelain prosthetic tooth implants, while simultaneously protecting surrounding tissues from damage.

A further object of the present invention is to provide a neutralizing barrier and methods for delivering a neutralizing barrier to provide for the neutralization of any hydrofluoric acid or other acid etching composition that came in contact with the barrier protecting the surrounding sulcular and gum tissues.

Finally, a further object is to provide a neutralizing barrier and methods for delivering a neutralizing barrier to provide a material which can be quickly and effectively rinsed away with water along with the etching composition in order to terminate the etching procedure, neutralize the acid relative to sanitary disposal concerns, and quickly clean the etched surface preparatory to subsequent bonding.

Additional objects and advantage of the invention will be set forth in the description which follows and in part will be obvious from the description, or may be learned by the practice of the invention. The objects and advantages of the invention may be realized and obtained by means of the compositions and methods particularly pointed out in the appended claims.

To achieve the foregoing objects, and in accordance with the invention as embodied and described herein, the present invention comprises a composition for forming a neutralizing barrier and methods for etching a tooth or prosthesis using the novel neutralizing barrier composition. The neutralizing barrier is preferably syringe-deliverable and is formed from a viscous caulking-type material comprising a matrix material and an acid neutralizer.

The matrix material can be any substance having a rheology such that a bead of the viscous caulking-type material will reliably and continuously adhere to the area of tooth surface comprising the perimeter of the area to be etched and not uncontrollably flow to unwanted areas. The matrix material preferably has a viscosity that is at least low enough to enable the matrix material to be syringe-deliverable. The caulking-type material is preferably sufficiently flowable to be able to flow into and fill all cracks and crevices of the tooth, where applied, while having a high enough yield stress and stickiness that the bead of caulk will remain in place in the desired configuration without flowing down the side of the tooth during an etching procedure. The neutralizing barrier preferably fills all cracks and crevices to prevent the etching composition from flowing under the barrier and changing the surrounding tissue.

The preferred matrix material comprises a silica-based gel formed by mixing fumed silica and water. Fumed silica-gel is particularly effective with acid etches containing hydrofluoric acid as the fumed silica can additionally react with and help to neutralize any hydrofluoric acid coming in contact with the neutralizing barrier. However, other gelling or thickening agents and appropriate acid neutralizing and fluoride ion binding agents can also be used. These include organic polymers and gums that can form stable gels. In addition, polyols can be used in addition and in some cases instead of the water.

The acid neutralizing agent is dispersed within the viscous caulking-type material in order to neutralize any acid that comes into contact with the barrier. This provides further protection of the surrounding sulcular and gum tissues. The neutralizer can be any material capable of neutralizing acids in acid etch solutions. The preferred acid neutralizer for use with an acid etch containing hydrofluoric acid includes sodium bicarbonate ($NaHCO_3$) and calcium carbonate ($CaCO_3$). Sodium bicarbonate is a highly effective acid neutralizer and calcium carbonate reacts with the fluoride ions to further neutralize their potential toxicity. For an acid etch comprising any acid other than hydrofluoric acid, the calcium carbonate is largely unnecessary, although it too will neutralize acid, although more slowly than sodium bicarbonate.

The neutralizing barrier is preferably water soluble so that it can be easily rinsed off by water. This allows for quick and efficient removal of both the etching composition and neutralizing barrier with water, which can then be removed by air aspiration and/or a drying agent preparatory to subsequent bonding to the tooth or prosthesis surface.

The method of the present invention is generally achieved by first delivering the neutralizing caulking-type material by means of a syringe for ease of application to quickly and efficiently form a neutralizing barrier at a desired area adjacent to or near the surface of the porcelain prosthesis or tooth being treated. This defines an inner etching area and an outer area to be protected from the etching composition. The syringe is usually equipped with an extended tip having an opening diameter that is commensurate for delivering a controlled yet effective barrier dimension.

Second, the etching composition is applied to the etching area by means of a syringe that is also equipped with a narrow tip. An etching composition suitable for etching a porcelain prosthesis typically includes hydrofluoric acid in a concentration of about 2–15% by weight, which remains in contact with the etching surface for a period of time sufficient to create the desired degree of etching. Finally, the etching composition and neutralizing barrier are removed by rinsing the tooth or prosthesis with an amount of water sufficient to completely rinse away both the etching composition and the neutralizing barrier, thereby terminating the etching procedure. After the etching area has been thoroughly rinsed, the treated tooth or prosthesis surface is optimally dried and further treated if necessary before a new prosthesis or resinous composite is bonded the etched tooth or prosthesis surface.

The above methods can also be used to protect surrounding tissues during the etching of enamel or dentin surfaces with acid etching compositions, such as phosphoric acid, citric acid, nitric acid, hydrochloric acid, etc.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawing depict only a typical embodiment of the invention and are not therefore to be considered to be limiting of its scope, the invention will be described and explained with additional specifity and detail through the use of the accompanying drawings in which.

DETAILED DESCRIPTION OF THE PREFERRED EMBODIMENTS

The present invention relates to preparing a tooth or porcelain prosthesis for bonding by etching the tooth or porcelain crown. More particularly, the present invention is directed to a syringe-deliverable neutralizing barrier and methods for creating a neutralizing barrier whereby an area on a tooth or porcelain crown is isolated for acid etching, while protecting the surrounding tissues from being irritated, damaged, or otherwise deleteriously affected by the acid etch.

Figure 1:
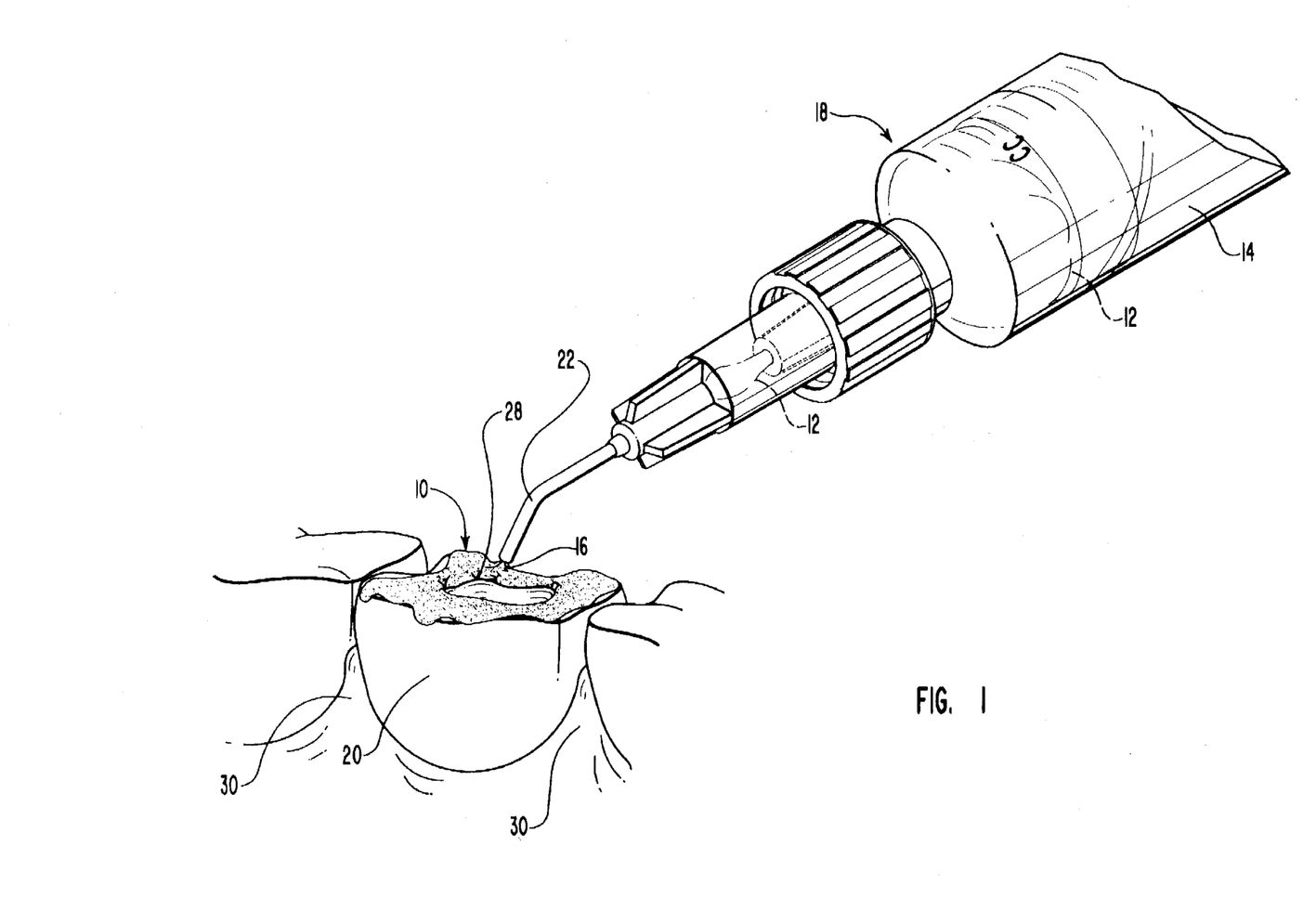
FIG. 1 is a perspective view of a syringe assembly delivering a neutralizing barrier onto the surface of a tooth.

FIG. 1 illustrates a neutralizing barrier 10 as a bead after the syringe-deliverable viscous caulking-type material 12 has been dispensed from the barrel 14 and out of the opening 16 of a syringe assembly 18 onto the surface of a tooth or porcelain prosthesis 20. Neutralizing barrier 10 is formed as syringe-deliverable caulking-type material 12 is applied to tooth or porcelain prosthesis 20. It is preferable to deliver caulking-type material 12 by syringe assembly 18 in order to provide an accurate and efficient application of neutralizing barrier 10. Syringe assembly 18 can be equipped with a specialized tip 22 to further enhance the ability to accurately form neutralizing barrier 10. It is also within the scope of the present invention, however, to place neutralizing barrier 10 on the surface of tooth or porcelain prosthesis 20 by any means known to one of ordinary skill in the art.

Caulking-type material 12 comprises a matrix material and an acid neutralizing agent. Caulking-type material 12 has a theology and viscosity such that it will adequately adhere to the surface of a tooth or porcelain prosthesis 20 or adjacent gum tissues where it is applied in a desired configuration of a neutralizing barrier 10. Caulking-type material 12 further has a rheology and viscosity such that it will adequately and substantially remain in the desired shape or configuration of neutralizing barrier 10 during the acid etching procedure. The viscosity and rheology of neutralizing barrier 10 also preferably enables neutralizing barrier 10 to flow into and substantially conform to the irregularities and contours of the surface of tooth 20 while being in intimate and continuous contact with the surface of a tooth or porcelain prosthesis 20. The viscosity and rheology of neutralizing barrier 10 also prevents significant migration of etching composition from the area defined by neutralizing barrier 10. Hence, neutralizing barrier 10 provides an impermeable border surrounding the area to be etched such that an etching composition is reliably maintained within the narrow confines of the designated etching area.

The caulking-type material 12 preferably has sufficient tackiness and sufficiently high internal cohesion and yield stress that neutralizing barrier 10 reliably adheres without significantly flowing out of the desired configuration after being applied. Caulking-type material 12 also preferably has a theology and a sufficiently low internal cohesion, viscosity, and yield stress to enable it to be dispensed by means of syringe having an opening that is conducive to delivering a bead of caulking material 12 having the desired dimensions.

Figure 2:
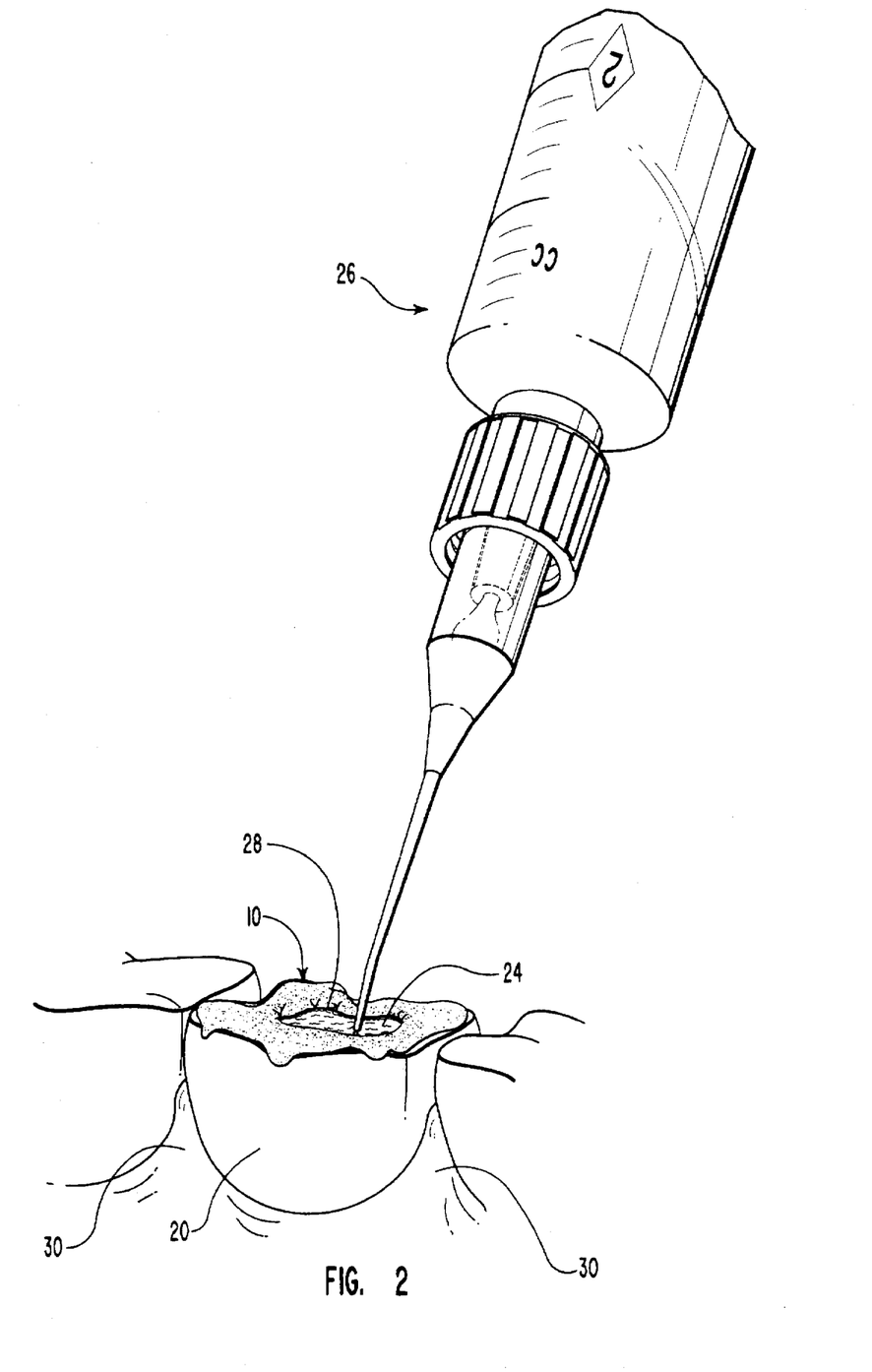
FIG. 2 is a perspective view of another syringe assembly containing acid etch, the acid etch being applied onto the etching area defined by the neutralizing barrier.

As shown in FIG. 2, an acid etch or etching composition 24 is preferably delivered by another syringe assembly 26 and applied onto the etching area 28 of tooth or porcelain prosthesis 20 after neutralizing barrier 10 has been positioned around the etching area 28. Of course, the acid etch 24 may also be applied by any means known to one of ordinary skill in the art.

Etching area 28 is thusly defined by the boundary or wall formed by neutralizing barrier 10. The flow of etching composition 24 is restricted to etching area 28 by neutralizing barrier 10 and from flowing underneath or around neutralizing barrier 10 because of the substantially intimate and continuous contact of neutralizing barrier 10 and the surface of tooth or porcelain prosthesis 20. Neutralizing barrier 10 protects the nearby gums and sulcular tissue 30 and other hard or soft tissues from etching composition 24, while only allowing etching of the area of the tooth that is desired to be etched (etching area 28) preparatory to subsequent bonding of a prosthesis or resinous composite material to the tooth or porcelain prosthesis 20.

Etching composition 24 can be any etching solution, gel or viscous liquid capable of etching a substrate, particularly a dental substrate such as a tooth, a porcelain prosthesis, or metal. Additionally, etching composition 24 can contain any acid which is useful for etching a dental substrate, such as a bridge or crown. The neutralizing barrier 10 can be used with any acid etching conditions, such as those used to treat dentin or enamel. The present invention is particularly useful in procedures that employ etching compositions containing hydrofluoric acid used to etch porcelain surfaces, such as existing prostheses. Neutralizing barrier 10 enables a hydrofluoric acid etching composition to be directly applied to porcelain prosthesis 20 in the patient's mouth, which procedure was previously far more difficult due to the dangers involved in using hydrofluoric acid in proximity to sensitive oral tissues. The ability to use a hydrofluoric acid etching composition in a patient's mouth facililates the ability to directly place a new crown or other prosthesis to the existing prosthesis, or indirectly place it in laboratory conditions. This eliminates or greatly reduces the need for removing porcelain prosthesis 20 in order to etch or furnace fire porcelain prosthesis 20, which is a common procedure.

The matrix or gel forming material with in viscous caulking-type material 12 may comprise an inorganic or organic material. The only criteria being that it be able to form a stable gel that will not prematurely break down when exposed to acids etches contemplated by the present invention. In the case where only weakly acid solutions are employed, gums and other polymers that might tend to breakdown in the presence of stronger acids may be employed. The matrix material preferably comprises the aforementioned inorganic or organic matrix or gel forming material dispersed within a liquid carrier such as water, polyols or other appropriate polar solvents, and mixtures thereof.

The optimal flow properties are described above as being a viscosity, theology, yield stress, internal cohesion and tacitness such that caulking-type material 12 is conducive to syringe delivery, yet such that neutralizing barrier 10 formed thereby is able to reliably, intimately and continuously adhere to the tooth surface and/or soft dental tissue, without substantially flowing after being placed in a desired configuration. Neutralizing barrier 10 is also preferably easily rinsed off by a solvent wash, such as water, to allow for subsequent bonding to the etched surface of tooth 14.

The inorganic or organic material which imparts the necessary viscosity, rheology, yield stress, internal cohesion and tackiness to the caulking-type material 12 and neutralizing barrier 10 when combined with a liquid carrier to form a matrix material is referred to herein as a thickener or gelling agent. The most preferred thickener is fumed silica and the most preferred matrix material is a silica-based aqueous gel formed by mixing fumed silica with water. One advantage of using fumed silica is its tendency to further neutralize an acid etch containing hydrofluoric acid, since silica and fluoride ions react to form a silical fluoride complex.

Examples of other suitable thickeners include other silica-based and non-silica-based inorganic thickeners or fillers and organic thickeners such as polysaccharide gums or natural or synthetic polymers. Examples of suitable inorganic thickeners or fillers in addition to fumed silica include ground silica gel, titanium dioxide, aluminum oxide, mixtures thereof, and the like. Examples of suitable organic thickeners, include but are not limited to, cellulose-based thickeners such as cellulosic ethers; polysaccharide gums such as xanthan gum, guar gum and gum arabic; and water-dispersible polymeric thickeners such as carboxypolymethylene. Included within the meaning of the foregoing organic thickeners are mixtures, derivatives, or equivalents of the foregoing. It is within the scope of the present invention to form a matrix material with more than one type of thickener. For example, fumed silica and xanthan gum or another organic filler can be intermixed with water.

The ratio of thickener to water can be any ratio as along as the resulting matrix material, when mixed with a neutralizing agent, forms a caulking-type material 12 having adequate viscosity and rheology, yield stress, internal cohesion and tackiness. When fumed silica is included in the mixture that forms the matrix material it is preferably included in a range from about 0.01% to about 25% by weight of the mixture.

Examples of liquid carriers include liquid hydrocarbons and water, preferably deionized water. It is also within the scope of the present invention to use a liquid carrier comprising a mixture of more than one type of liquid. Examples of liquid hydrocarbons include, but are not limited to, mineral oils and polyols. Examples of polyols include, but are not limited to, polypropylene glycol, propylene glycol, polyethylene glycol, glycerol, sorbitol, mixtures thereof and derivatives thereof. Ethylene glycol would work but it is generally unsuitable for oral medicaments due to its toxicity if ingested.

It is also within the scope of the present invention to form caulking type material 12 from a mixture of a viscous liquid carrier and an acid neutralizing agent with or without the aforementioned thickeners. Accordingly, the matrix material may be only a viscous liquid carrier. Any viscous liquid carrier capable of imparting the necessary viscosity and rheology to the caulking material is within the scope of the present invention. The viscous liquid carrier is preferably a hydrocarbon liquid. Suitable viscous hydrocarbon liquid carriers include, but are not limited to, polyethylene glycols, polypropylene glycols, sorbitol, mixtures thereof and derivatives thereof having an appropriate molecular weight to impart the necessary viscosity and rheology to the caulking-type material.

The acid neutralizing agent which is dispersed in caulking-type material 12 may comprise any material capable of neutralizing the acids used in acid etches such as hydrofluoric acid, phosphoric acid, sulfuric acid and hydrochloric acid. The acid neutralizing agent is preferably pH buffered. Examples of acid neutralizing agents within the scope of this invention include all carbonates and their salts. The acid neutralizing agent preferably comprises sodium bicarbonate ($NaHCO_3$), which is water soluble and highly reactive with most acids. Calcium carbonate ($CaCO_3$) is also preferably included in the acid neutralizing agent when used to neutralize an acid etch containing hydrofluoric acid. Calcium carbonate is slower to react than sodium bicarbonate; however, it reacts with the fluoride ions to form an insoluble salt, thereby further reducing the etching and/or toxic activity of the hydrofluoric acid.

When caulking-type material 12 is used to form a neutralizing barrier 10 for neutralizing an acid etch containing hydrofluoric acid, sodium bicarbonate is preferably included in a range from about 0.5% to about 50% by weight of the mixture, more preferably in a range from about 5% to about 25% by weight of the mixture, and most preferably in a range from about 7% to about 15% by weight of the mixture. Additionally, when caulking-type material 12 is used to form a neutralizing barrier 10 for neutralizing an acid etch containing hydrofluoric acid, calcium carbonate is preferably included in a range from about 0.2% to about 45% by weight of the mixture or caulking-type material 12, more preferably in a range from about 1% to about 20% by weight of the mixture, and most preferably in a range from about 2% to about 10% by weight of the mixture.

One preferred embodiment of caulking-type material 12 used to form a neutralizing barrier 10 for neutralizing an acid etch containing hydrofluoric acid comprises fumed silica, about 10% sodium bicarbonate by weight of the mixture, about 6% calcium carbonate by weight of the mixture, with the balance comprising deionized water. A preferred embodiment of the caulking-type material 12 used to form a neutralizing barrier 10 for neutralizing an acid etch containing hydrofluoric acid also comprises an organic thickener such as xanthan gum in a range from about 0.01% to about 2% by weight of the mixture and most preferably in an amount of about 0.08% by weight of the mixture. Xanthan gum provides desired wetting properties and acts as a thickening and tackifying agent to improve the viscosity, flow properties, and adhesion of the caulking-type material 112. The preferred embodiment of caulking-type material 12 for neutralizing an acid etch containing hydrofluoric acid further comprises a pigment to increase the visibility of neutralizing barrier 10 for accurate placement on the surface of tooth or porcelain prosthesis 20, or adjacent soft tissues. Pigments are preferably included in a range from about 0.01% to about 2% by weight of the mixture.

Another preferred embodiment of caulking-type material 12 used to form a neutralizing barrier 10 for neutralizing an acid etch containing hydrofluoric acid comprises by weight about 4% fumed silica, 30% propylene glycol, 0.08% xanthan gum, 46.62% distilled water, 4.5% calcium carbonate, 10.2 sodium bicarbonate, and 4.6% purple pigment.

The present invention can be part of a kit for etching tooth surfaces comprising neutralizing barrier 10 and etching composition 24. Neutralizing barrier 10 and etching composition 24 can be delivered by a syringe or by other means onto the surface of tooth or porcelain prosthesis 20. Etching composition 24 can be a hydrofluoric acid etching compositions or any other acidic solution capable of effectively etching the surface(s) of tooth or porcelain prosthesis 20.

The concentration of hydrofluoric acid in a hydrofluoric acid etching composition may vary widely and is adjusted according to the desired speed and intensity of the etch being performed. The hydrofluoric acid etching composition 24 may also include xanthan gum to increase the viscosity and tackiness, and pigment to increase the visibility of etching composition 24.

The method for preparing a tooth or porcelain prosthesis for bonding according to the present invention is generally achieved by first preparing a caulking-type material that is preferably syringe-deliverable as a neutralizing barrier including a matrix material and acid neutralizing agent, preferably placing the caulking-type material into barrel 14 of syringe apparatus 16, delivering neutralizing barrier 10 onto a surface of tooth or porcelain prosthesis 20 in a desired configuration in close proximity to an area of tooth or porcelain prosthesis 20 requiring etching. In this manner, etching area 28 and an area of the tissue to be protected from a subsequently applied etching composition are defined. Thereafter, the etching composition 24 is applied to etching area 28 for a period of time great enough to effect the desired mount of etching of the moth or prosthetic porcelain surface. The surface is usually sufficiently etched after about two minutes or less of contact when a 9% hydrofluoric acid etching composition is applied. Finally, the neutralizing barrier 10 and etching composition 24 are rinsed from tooth 20 with water or an aqueous solvent, thereby terminating the etching process. After the etching area has been rinsed, it is allowed to dry before a prosthesis is bonded onto tooth 20. This can be accelerated by air aspiration and/or the application of a drying agent.

Neutralizing barrier 10 prevents etching composition 24 from spreading beyond etching area 28 defined by neutralizing barrier 10, thereby protecting gums and sulcular tissue 30 in close proximity to neutralizing barrier 10 from damage or irritation. The neutralizing barrier 10 around the area to be etched also reduces the area of tooth or porcelain prosthesis 20 that is unnecessarily etched and the amount of etching composition 24 needed, as neutralizing barrier 10 restricts etching composition 24 to only the area requiring etching. Additionally, the etching procedure is thusly rendered much more efficient and safe compared to prior methods. The increase in safety and protection provided by neutralizing barrier 10 allows for the use of adequately high acid concentrations, which can increase the efficiency of acid etching as less exposure time is necessary. Neutralizing barrier can be quickly and effectively rinsed away with water along with etching composition 24 in order to terminate the etching procedure and quickly clean the etched surface preparatory to subsequent bonding. When mixed with the acid etching composition and water, the material comprising the neutralizing barrier neutralizes any unreacted acid before it is washed down the drain.

EXAMPLES OF THE PREFERRED EMBODIMENT

Examples are provided of the present invention to compare the properties of the compositions by varying the content of the components. Examples 2–6 are hypothetical examples of the present invention. While examples 2–6 are hypothetical in nature they are based upon actual mix designs that have been tested or contemplated and are presented in this form in order to more completely illustrate the nature of the invention.

Example 1

A caulking-type material used to form a neutralizing barrier to protect surrounding tissues from an acid etching solution was formed from the following components:

| Component | Percent by Weight of the Mixture |
| --- | --- |
| Distilled water | 79.5 |
| Sodium bicarbonate | 10.2 |
| Calcium carbonate | 4.5 |
| Fumed silica | 4.42 |
| Xanthan gum | 0.08 |
| Purple pigment | 1.3. |

After the caulking-type material was prepared, it was placed in a syringe assembly having an opening less than about 4 mm in diameter and delivered onto a porcelain crown surface to define an etching area. The caulking material had a viscosity and theology such that it reliably adhered to the crown surface where it was applied, substantially conformed to the irregularities of the crown surface, and substantially remained in the shape of the desired neutralizing barrier after being placed in a desired configuration. An etching solution including 9% HF was applied to the etching area in order to etch the porcelain surface. The neutralizing barrier confined the etching solution within the etching area, while neutralizing any acid which came into direct contact with the neutralizing barrier. Both the acid etch and neutralizing barrier were easily rinsed away with water upon termination of the etching procedure.

Example 2

A caulking-type material used to form a neutralizing barrier to protect surrounding tissues from an acid etching solution is formed from following components:

| Component | Percent by Weight of the Mixture |
| --- | --- |
| Distilled water | 81.38 |
| Sodium bicarbonate | 10.2 |
| Calcium carbonate | 4.5 |
| Fumed silica | 2.42 |
| Xanthan gum | 0.2 |
| Pigment | 1.3. |

After the caulking-type material is prepared, it is placed in a syringe assembly and delivered onto a porcelain crown surface to define an etching area. The tackiness of the caulking-type material would be expected to be greater than the composition in Example 1 due to the increased xanthan gum content. The caulking-type material would also be expected to have a viscosity and rheology such that it reliably adheres to the crown surface where it is applied, substantially conforms to the irregularities of the crown surface, and substantially remains in the shape of the desired neutralizing barrier after being placed in a desired configuration. An etching solution including 9% HF is applied to the etching area in order to etch the porcelain surface. The neutralizing barrier confines the etching solution within the etching area, while neutralizing any acid which comes into direct contact with the neutralizing barrier. Both the acid etch and neutralizing barrier are easily rinsed away with water upon termination of the etching procedure.

Example 3

A caulking-type material used to form a neutralizing barrier to protect surrounding tissues from an acid etching solution is formed from following components:

| Component | Percent by Weight of the Mixture |
|---|---|
| Distilled water | 72.2 |
| Sodium bicarbonate | 5 |
| Calcium carbonate | 19 |
| Fumed silica | 2.42 |
| Xanthan gum | 0.08 |
| Pigment | 1.3. |

After the caulking-type material is prepared, it is placed in a syringe assembly and delivered onto a porcelain crown surface to define etching areas. The caulking-type material would be expected to have a viscosity and rheology such that it reliably adheres to the crown surface where it is applied, substantially conforms to the irregularities of the crown surface, and substantially remains in the shape of the desired neutralizing barrier after being placed in a desired configuration. An etching solution including 9% HF is applied to the etching area in order to etch the porcelain surface. The neutralizing barrier confines the etching solution within the etching area, while neutralizing any acid which comes into direct contact with the neutralizing barrier. Due to the high calcium carbonate content, the neutralizing barrier is particularly effective in neutralizing any hydrofluoric acid coming into contact with the neutralizing barrier. Both the acid etch and neutralizing barrier are easily rinsed away with water upon termination of the etching procedure.

Example 4

A caulking-type material used to form a neutralizing barrier to protect surrounding tissues from an acid etching solution is formed from following components:

| Component | Percent by Weight of the Mixture |
|---|---|
| Distilled water | 69.18 |
| Sodium bicarbonate | 25 |
| Calcium carbonate | 1 |
| Fumed silica | 3.42 |
| Xanthan gum | 0.1 |
| Pigment | 1.3. |

After the caulking-type material is prepared, it is placed in a syringe assembly and delivered onto a porcelain crown surface to define an etching area. The caulking-type material would be expected to have a viscosity and rheology such that it reliably adheres to the crown surface where it is applied, substantially conforms to the irregularities of the crown surface, and substantially remains in the shape of the desired neutralizing barrier after being placed in a desired configuration. An etching solution including 9% HF is applied to the etching area in order to etch the porcelain surface. The neutralizing barrier confines the etching solution within the etching area, while neutralizing any acid which comes into direct contact with the neutralizing barrier. Although, the neutralizing barrier would sufficiently neutralize acids coming into contact with the neutralizing barrier, it would not be expected to be as effective as the neutralizing barrier of Example 1 for neutralizing hydrofluoric acid due to the lower content of calcium carbonate and silica. Both the acid etch and neutralizing barrier are easily rinsed away with water upon termination of the etching procedure.

Example 5

A caulking-type material used to form a neutralizing barrier to protect surrounding tissues from an acid etching solution is formed from following components:

| Component | Percent by Weight of the Mixture |
|---|---|
| Distilled water | 87.7 |
| Sodium bicarbonate | 1 |
| Calcium carbonate | 8 |
| Fumed silica | 0.5 |
| Xanthan gum | 1.8 |
| Pigment | 1.3. |

After the caulking material is prepared, it is placed in a syringe assembly and delivered onto a porcelain crown surface to define an etching area. The caulking material would be expected to have a viscosity and rheology such that it reliably adheres to the crown surface where it is applied, substantially conforms to the irregularities of the crown surface, and substantially remains in the shape of the desired neutralizing barrier after being placed in a desired configuration. An etching solution including 9% HF is applied to the etching area in order to etch the porcelain surface. The neutralizing barrier confines the etching solution within the etching area, while neutralizing any acid which comes into direct contact with the neutralizing barrier. Although, the neutralizing barrier would sufficiently neutralize acids coming into contact with the neutralizing barrier, it would not be expected to be as effective as the neutralizing barriers of the previous examples for neutralizing hydrofluoric acid due to the lower content of calcium carbonate, sodium bicarbonate and silica. Both the acid etch and neutralizing barrier are easily rinsed away with water upon termination of the etching procedure.

Example 6

A caulking-type material used to form a neutralizing barrier to protect surrounding tissues from an acid etching solution is formed from following components:

| Component | Percent by Weight of the Mixture |
|---|---|
| Distilled water | 54.12 |
| Sodium bicarbonate | 20 |
| Calcium carbonate | 24 |
| Fumed silica | 0.5 |
| Xanthan gum | 0.08 |
| Pigment | 1.3. |

After the caulking-type material is prepared, it is placed in a syringe assembly and delivered onto a porcelain crown surface to define an etching area. The caulking-type material is less viscous than the neutralizing barriers of the previous examples, however, it still reliably adheres to the crown surface where it is applied, substantially conforms to the irregularities of the crown surface, and substantially remains in the shape of the desired neutralizing barrier after being placed in a desired configuration. An etching solution including 9% HF is applied to the etching area in order to etch the porcelain surface. The neutralizing barrier confines the etching solution within the etching area, while neutralizing any acid which comes into direct contact with the neutralizing barrier. Due to the high calcium carbonate and sodium bicarbonate content, the neutralizing barrier is particularly effective in neutralizing any hydrofluoric acid coming into contact with the neutralizing barrier. Both the acid etch and neutralizing barrier are easily rinsed away with water upon termination of the etching procedure.

Example 7

A caulking-type material used to form a neutralizing barrier to protect surrounding tissues from an acid etching solution is formed from following components:

| Component | Percent by Weight of the Mixture |
| --- | --- |
| Xanthan gum | 0.08 |
| Distilled water | 78.5 |
| Purple pigment | 2.3 |
| Sodium bicarbonate | 10.2 |
| Calcium carbonate | 4.5 |
| Fumed aluminum oxide | 4.42 |

The caulking-type material would be expected to be slightly less viscous than the caulking-type material produced in Example 1.

Example 8

A caulking-type material used to form a neutralizing barrier to protect surrounding tissues from an acid etching solution is formed from following components:

| Component | Percent by Weight of the Mixture |
| --- | --- |
| Purple pigment | 4.6 |
| Sodium bicarbonate | 31.0 |
| Calcium carbonate | 18.0 |
| Anhydrous glycerol | 46.4 |

The caulking-type material would be expected to adhere to a tooth surface with minimal flow.

Example 9

A caulking-type material used to form a neutralizing barrier to protect surrounding tissues from an acid etching solution is formed from following components:

| Component | Percent by Weight of the Mixture |
| --- | --- |
| Propylene glycol | 76.7 |
| Fumed silica | 4.0 |
| Purple pigment | 4.6 |
| Sodium bicarbonate | 10.2 |
| Calcium carbonate | 4.5 |

The caulking-type material would be expected to have comparable viscosity and adhesion compared to the caulking-type material produced in Example 1.

Example 10

A caulking-type material used to form a neutralizing barrier to protect surrounding tissues from an acid etching solution is formed from following components:

| Component | Percent by Weight of the Mixture |
| --- | --- |
| Distilled water | 46.7 |
| Propylene glycol | 30.0 |
| Purple pigment | 4.6 |
| Sodium bicarbonate | 10.2 |
| Calcium carbonate | 4.5 |
| Fumed aluminum oxide | 4.0 |

The caulking-type material would be expected to be slightly less viscous than the caulking-type material produced in Example 1.

SUMMARY

From the foregoing, it will be appreciated that the present invention provides novel compositions and methods for a neutralizing barrier and methods for delivering the neutralizing barrier.

In particular, the present invention provides a neutralizing barrier and methods for delivering a neutralizing barrier which protect hard and soft tissues surrounding a tooth or prosthetic implant being etched.

The present invention also provides a quickly and easily applied syringe-deliverable neutralizing barrier and methods for delivering the neutralizing barrier to maintain an etching solution within the area of the tooth or prosthetic porcelain surface that is desired to be etched.

The present invention further provides a neutralizing barrier and methods for delivering a neutralizing barrier in order to directly apply hydrofluoric acid to existing porcelain prosthetic tooth implants, while simultaneously protecting surrounding tissues from damage or isolating them from unwanted exposure.

Further, the present invention provides a neutralizing barrier and methods for delivering a neutralizing barrier to neutralize any hydrofluoric acid or other acid etching solution that comes in contact with the barrier protecting the surrounding tooth, sulcular, or gum tissues.

Finally, the present invention provides a neutralizing barrier and methods for delivering a neutralizing barrier to yield a material which can be quickly and effectively rinsed away with water along with the etching solution in order to terminate the etching procedure, neutralize the acid etch, and quickly clean the etched surface preparatory to subsequent bonding.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A caulking-type material for application to a dental substrate to form a neutralizing barrier that confines an etching composition to a defined area on the dental substrate during an etching procedure, the caulking-type material comprising a mixture product of a matrix material and an acid neutralizing agent, the matrix material comprising at least a carrier, the caulking-type material having a viscosity and rheology such that during the etching procedure the caulking-type material (a) will adhere to the dental substrate where it is applied in a desired configuration of the neutralizing barrier, (b) will substantially remain in the desired configuration during the acid etching procedure, and (c) will prevent significant migration of an etching composition from the defined area.

2. A caulking-type material as defined in claim 1, wherein the matrix material further comprises a thickener.

3. A caulking-type material as defined in claim 2, wherein the thickener is fumed silica.

4. A caulking-type material as defined in claim 2, wherein the thickener is selected from the group consisting of inorganic thickeners and organic thickeners.

5. A caulking-type material as defined in claim 2, wherein the thickener is selected from the group consisting of titanium dioxide and aluminum oxide.

6. A caulking-type material as defined in claim 2, wherein the thickener is selected from the group consisting of cellulose-based thickeners, polysaccharide gums and water dispersible polymeric thickeners, mixtures thereof and derivatives thereof.

7. A caulking-type material as defined in claim 1, wherein the carrier is a liquid carrier selected from the group consisting of water and a liquid hydrocarbon carrier.

8. A caulking-type material as defined in claim 7, wherein the liquid hydrocarbon carrier is selected from the group consisting of mineral oil and a polyol.

9. A caulking-type material as defined in claim 8, wherein the polyol is selected from the group consisting of polypropylene glycol, propylene glycol, polyethylene glycol, glycerol, sorbitol, mixtures thereof and derivatives thereof.

10. A caulking-type material as defined in claim 1, wherein the carrier is a viscous liquid carrier.

11. A caulking-type material as defined in claim 10, wherein the viscous liquid carrier is a hydrocarbon viscous liquid carrier.

12. A caulking-type material as defined in claim 1, wherein the acid neutralizing agent comprises a carbonate salt.

13. A caulking-type material as defined in claim 1, wherein the acid neutralizing agent comprises a bicarbonate salt.

14. A caulking-type material as defined in claim 12, wherein the carbonate salt includes calcium carbonate.

15. A caulking-type material as defined in claim 13, wherein the bicarbonate salt includes sodium bicarbonate.

16. A caulking-type material as defined in claim 1, wherein the acid neutralizing agent comprises a mixture including a carbonate salt and a bicarbonate salt.

17. A caulking-type material as defined in claim 1, wherein the caulking-type material is syringe deliverable.

18. A method for forming a neutralizing barrier to confine an etching composition to a defined area of a dental substrate during an etching procedure, the method comprising the steps of:
 (a) providing a caulking-type material comprising a mixture product of a matrix material and an acid neutralizing agent, the matrix material comprising at least a carrier; and
 (b) delivering the caulking-type material onto the dental substrate to form the neutralizing barrier in a desired configuration in order to define an etching area for subsequent application of an etching composition.

19. A method for forming a neutralizing barrier to confine an etching composition to a defined area of a dental substrate during an etching procedure the method comprising the steps of:
 (a) providing a caulking-type material comprising a mixture product of a matrix material and an acid neutralizing agent, the matrix material comprising at least a carrier; and
 (b) placing the caulking-type material into a syringe assembly; and
 (c) delivering the caulking-type material from the syringe assembly onto the dental substrate to form the neutralizing barrier in a desired configuration in order to define an etching area for subsequent application of an etching composition.

20. A method for etching a defined area of a dental substrate as defined in claim 19, further including the step of rinsing away the etching composition and neutralizing barrier upon completion of the etching procedure.

21. A method for etching a defined area of a dental substrate comprising the steps of:
 (a) providing a caulking-type material comprising a mixture product of a matrix material and an acid neutralizing agent, the matrix material comprising at least a carrier;
 (b) delivering the caulking-type material onto the dental substrate to form the neutralizing barrier in a desired configuration in order to define an etching area during an etching procedure; and
 (c) applying an etching composition within the etching area in order to etch the etching area of the dental substrate.

22. A method for etching a defined area of a dental substrate as defined in claim 21, further including the steps of:
 intermixing the etching composition and the neutralizing barrier to neutralize the etching composition after acid etching the dental substrate in the etching area; and
 rinsing away the intermixed etching composition and neutralizing barrier.

23. A method for etching a defined area of a dental substrate comprising the steps of:
 (a) providing a syringe-deliverable caulking-type material comprising a mixture product of a matrix material and an acid neutralizing agent, the matrix material comprising at least a carrier;
 (b) delivering the caulking-type material from a syringe assembly onto the dental substrate to form the neutralizing barrier in a desired configuration in order to define an etching area during an etching procedure; and
 (c) applying an etching composition within the etching area in order to etch the etching area of the dental substrate.

24. A method for etching a defined area of a dental substrate as defined in claim 23, further including the steps of:
 intermixing the etching composition and the neutralizing barrier to neutralize the etching composition after acid etching the dental substrate in the etching area; and
 rinsing away the intermixed etching composition and neutralizing barrier.

25. A kit for etching a defined area of a dental substrate comprising:
 (a) a caulking-type material comprising a mixture product of a matrix material and an acid neutralizing agent, the matrix material including at least a carrier, the caulking-type material having a viscosity and rheology such that during an etching procedure the caulking-type material (1) will adhere to the dental substrate where it is applied in a desired configuration of the neutralizing barrier, (2) will substantially remain in the desired configuration, and (3) will prevent significant migration of etching composition from the defined area; and
 (b) an acid etching composition.

26. A kit for etching a defined area of a dental substrate as defined in claim 25, wherein the acid etching composition includes hydrofluoric acid.

27. A kit for etching a defined area of a dental substrate as defined in claim 25, wherein the caulking-type material is syringe deliverable.

28. A caulking-type material for application to a dental substrate to form a neutralizing barrier that confines an etching composition to a defined area on the dental substrate during an etching procedure, the caulking-type material comprising
 a mixture product of a matrix material and an acid neutralizing agent,
 wherein the matrix material is at least a viscous liquid hydrocarbon selected from the group consisting of polyethylene glycol, polypropylene glycol, sorbitol, mixtures and derivatives thereof, and wherein the acid neutralizing agent is selected from the group consisting of carbonates and carbonate salts.

29. A caulking-type material for application to a dental substrate to form a neutralizing barrier that confines an etching composition to a defined area on the dental substrate during an etching procedure, the caulking-type material comprising a mixture product of a matrix material and an acid neutralizing agent,
wherein the matrix material is a mixture product of a thickener and a carrier, and
wherein the acid neutralizing agent is selected from the group consisting of carbonates and carbonate salts.

30. A caulking-type material as defined in claim 29, wherein the thickener is fumed silica.

31. A caulking-type material as defined in claim 29, wherein the thickener is selected from the group consisting of titanium dioxide and aluminum oxide.

32. A caulking-type material as defined in claim 29, wherein the thickener is selected from the group consisting of cellulose-based thickeners, polysaccharide gums and water dispersible polymeric thickeners, mixtures thereof and derivatives thereof.

33. A caulking-type material as defined in claim 29, wherein the carrier is a liquid carrier selected from the group consisting of water and a liquid hydrocarbon carrier.

34. A caulking-type material for application to a dental substrate to form a neutralizing barrier that confines an etching composition to a defined area on the dental substrate during an etching procedure, the caulking-type material comprising a mixture product of a matrix material and an acid neutralizing agent,
wherein the matrix material is a mixture product of an organic thickener and a carrier.

35. A caulking-type material as defined in claim 34, wherein the organic thickener is selected from the group consisting of cellulose-based thickeners, polysaccharide gums and water dispersible polymeric thickeners, mixtures thereof and derivatives thereof.

36. A caulking-type material as defined in claim 34, wherein the carrier is a liquid carrier selected from the group consisting of water and a liquid hydrocarbon carrier.

37. A caulking-type material as defined in claim 34, wherein the acid neutralizing agent is selected from the group consisting of carbonates and carbonate salts.

38. A caulking-type material for application to a dental substrate to form a neutralizing barrier that confines an etching composition to a defined area on the dental substrate during an etching procedure, the caulking-type material comprising a mixture product of a matrix material and an acid neutralizing agent,
wherein the matrix material is a mixture product of an inorganic thickener and water.

39. A caulking-type material as defined in claim 38, wherein the inorganic thickener is fumed silica.

40. A caulking-type material as defined in claim 38, wherein the inorganic thickener is selected from the group consisting of titanium dioxide and aluminum oxide.

41. A caulking-type material as defined in claim 38, wherein the acid neutralizing agent is selected from the group consisting of carbonates and carbonate salts.

* * * * *

UNITED STATES PATENT AND TRADEMARK OFFICE
CERTIFICATE OF CORRECTION

PATENT NO. : 5,722,833
DATED : Mar. 3, 1998
INVENTOR(S) : Dan E. Fischer

It is certified that error appears in the above-identified patent and that said Letters Patent is hereby corrected as shown below:

Col. 2, line 13, after "somewhat" delete --to--

Col. 3, line 29, after "that" change "came" to --comes--

Col. 4, line 58, after "bonded" insert --to--

Col. 5, line 46, after "a" change "theology" to --rheology--

Col. 6, line 3, after "a" change "theology" to --rheology--

Col. 6, line 5, before "syringe" insert --a--

Col. 6, line 45, after "prosthesis" change "to" to --on--

Col. 6, line 50, after "material" change "with in" to --within--

Col. 6, line 52, after "it" change "be" to --is--

Col. 6, line 54, after "to" change "acids" to --acid--

Col. 6, line 64, after "viscosity," change "theology" to --rheology--

Col. 6, line 65, before "such" change "tacitness" to --tackiness--

Col. 7, line 5, after "tooth" change "14" to --20--

Col. 8, line 47, before "The" change "112" to --12--

UNITED STATES PATENT AND TRADEMARK OFFICE
CERTIFICATE OF CORRECTION

Page 2 of 2

PATENT NO. : 5,722,833
DATED : Mar. 3, 1998
INVENTOR(S) : Dan E. Fischer

It is certified that error appears in the above-identified patent and that said Letters Patent is hereby corrected as shown below:

Col. 8, line 66, before "or" change "compositions" to --composition--

Col. 9, line 14, after "apparatus" change "16" to --18--

Col. 9, line 22, before "of" change "mount" to --amount--

Col. 9, line 22, after "the" change "moth" to --tooth--

Col. 10, line 17, after "and" change "theology" to --rheology--

Col. 11, line 47, after "and" change "theology" to --rheology--

Signed and Sealed this

Sixteenth Day of February, 1999

Attest:

*Attesting Officer*

*Acting Commissioner of Patents and Trademarks*